US011869641B2

(12) United States Patent
Kurfirst et al.

(10) Patent No.: US 11,869,641 B2
(45) Date of Patent: Jan. 9, 2024

(54) SYSTEMS AND METHODS FOR DETERMINING WHETHER AN INDIVIDUAL IS SICK BASED ON MACHINE LEARNING ALGORITHMS AND INDIVIDUALIZED DATA

(71) Applicant: Aetna Inc., Hartford, CT (US)

(72) Inventors: Dwayne Kurfirst, Hartford, CT (US); Robert E. Bates, III, Hartford, CT (US)

(73) Assignee: Aetna Inc., Hartford, CT (US)

( * ) Notice: Subject to any disclaimer, the term of this patent is extended or adjusted under 35 U.S.C. 154(b) by 564 days.

(21) Appl. No.: 17/119,982

(22) Filed: Dec. 11, 2020

(65) Prior Publication Data

US 2022/0189591 A1 Jun. 16, 2022

(51) Int. Cl.
*G16H 10/60* (2018.01)
*G06Q 10/0635* (2023.01)
*G06N 20/00* (2019.01)
*G06F 18/214* (2023.01)

(52) U.S. Cl.
CPC ......... *G16H 10/60* (2018.01); *G06F 18/2148* (2023.01); *G06N 20/00* (2019.01); *G06Q 10/0635* (2013.01)

(58) Field of Classification Search
CPC ........ G16H 10/60; G16H 30/20; G16H 30/40; G16H 40/63; G16H 40/67; G16H 50/20; G16H 50/70; G06F 18/2148; G06N 20/00; G06Q 10/0635; G06V 40/174; G10L 17/26; G10L 25/66
See application file for complete search history.

(56) References Cited

U.S. PATENT DOCUMENTS

| 10,824,852 | B1 * | 11/2020 | Zhang | G06V 10/82 |
|---|---|---|---|---|
| 2019/0272925 | A1 * | 9/2019 | Barrett | G16H 50/80 |
| 2019/0385711 | A1 * | 12/2019 | Shriberg | G16H 10/20 |
| 2020/0381130 | A1 * | 12/2020 | Edwards | G10L 15/16 |
| 2022/0189591 | A1 * | 6/2022 | Kurfirst | G06N 20/00 |

\* cited by examiner

*Primary Examiner* — Md K Talukder
(74) *Attorney, Agent, or Firm* — Leydig, Voit & Mayer, Ltd.

(57) ABSTRACT

In some instances, a user device for determining whether an individual is sick is provided. The user device is configured to obtain a facial image of an individual; obtain an audio file comprising a voice recording of the individual; determine a facial recognition confidence value associated with whether the individual is sick based on inputting the facial image into a facial recognition machine learning dataset that is individualized for the individual; determine a voice recognition confidence value associated with whether the individual is sick based on inputting the audio file into a voice recognition machine learning dataset that is individualized for the individual; determine whether the individual is sick based on the facial recognition confidence value and the voice recognition confidence value; and causing display of a prompt indicating whether the individual is sick.

24 Claims, 6 Drawing Sheets

SYSTEMS AND METHODS FOR DETERMINING WHETHER AN INDIVIDUAL IS SICK BASED ON MACHINE LEARNING ALGORITHMS AND INDIVIDUALIZED DATA

BACKGROUND

Impacts of viruses and other diseases are significant even during a typical flu season and the prevention of another global pandemic is a desire shared by many people as well as enterprise organizations. One of the most common ways diseases spread is through the workplace. For example, an individual may be feeling unwell, but may be unsure as to whether they are actually sick. For instance, they may attribute their unease to allergies, sleep deprivation, grogginess when waking up, and/or other factors rather than identifying that they are actually sick. As such, the individuals may go into work, and if they are sick, then they may spread the disease to others within the workplace. This may lead to an entire office space being infected, which may cause projects to be delayed and/or other severe drawbacks. Traditionally, temperature checks may be used to determine whether an individual is sick. However, these temperature checks are typically inaccurate on their own as a person's body temperature may rise and fall depending on external conditions (e.g., the temperature outside), which may lead individuals into a false sense of security. Accordingly, there remains a technical need to alert individuals that they are sick such that they may stay home and not infect others.

SUMMARY

In some examples, the present application may use machine learning (e.g., artificial intelligence) algorithms, models, and/or datasets to determine whether an individual is sick and/or infectious. For example, a user device (e.g., a smartphone) may receive images and/or voice recordings associated with an individual. The images may be images of the individual's face and the voice recordings may be audio recordings of the individual saying a phrase (e.g., "Mary had a little lamb"). The user device may train machine learning datasets based on the received images and/or voice recordings such that the machine learning datasets are individualized for the particular individual. By individualizing the machine learning datasets for the particular individual, the machine learning datasets may better predict and/or determine whether the individual is actually sick. After training the machine learning datasets, the user device may receive a new image and a new voice recording associated with the individual. The user device may input the new image and voice recording into the trained machine learning datasets to determine whether the individual is actually sick. Subsequently, the user device may display an alert of the determination or provide information indicating the determination to a second device.

In one aspect, a user device comprises one or more processors; and a non-transitory computer-readable medium having processor-executable instructions stored thereon. The processor-executable instructions, when executed, facilitate: obtaining a facial image of an individual; obtaining an audio file comprising a voice recording of the individual; determining a facial recognition confidence value associated with whether the individual is sick based on inputting the facial image into a facial recognition machine learning dataset that is individualized for the individual; determining a voice recognition confidence value associated with whether the individual is sick based on inputting the audio file into a voice recognition machine learning dataset that is individualized for the individual; determining whether the individual is sick based on the facial recognition confidence value and the voice recognition confidence value; and causing display of a prompt indicating whether the individual is sick.

Examples may include one of the following features, or any combination thereof. For instance, in some examples, the user device further comprises an image capturing device. The processor-executable instructions, when executed, further facilitate: using the image capturing device to obtain training data comprising a plurality of facial images of the individual; and individualizing the facial recognition machine learning dataset for the individual based on training the facial recognition machine learning dataset using the plurality of facial images of the individual.

In some instances, the user device further comprises a voice recording device. The processor-executable instructions, when executed, further facilitate: using the voice recording device to obtain training data comprising a plurality of voice recordings of the individual; and individualizing the voice recognition machine learning dataset for the individual based on training the voice recognition machine learning dataset using the plurality of voice recordings of the individual.

In some variations, the processor-executable instructions, when executed, further facilitate: receiving, from a wearable device and at a first instance in time, first sensor information indicating first health characteristics associated with the individual; generating a baseline health model of the individual based on the first sensor information, and wherein determining whether the individual is sick is further based on the baseline health model.

In some examples, the processor-executable instructions, when executed, further facilitate: receiving, from the wearable device and at a second instance in time that is subsequent to the first instance in time, second sensor information indicating second health characteristics associated with the individual; and determining one or more health characteristic confidence values based on comparing the second sensor information with the generated baseline health model, wherein determining whether the individual is sick is further based on the one or more health characteristic confidence values.

In some instances, the first and second health characteristics comprises one or more of an oxygen level of the individual, a temperature reading of the individual, a pulse rate of the individual, and a humidity value associated with the individual.

In some variations, the processor-executable instructions, when executed, further facilitate: receiving, from the wearable device and at a third instance in time, third sensor information indicating third health characteristics associated with the individual; based on comparing the third health characteristics with the first health characteristics, causing display of a second prompt requesting user feedback associated with updating the baseline health model; and in response to the user feedback indicating for the baseline health model to be updated, updating the baseline health model using the third health characteristics.

In some examples, determining the facial recognition confidence value comprises: inputting the facial image into the facial recognition machine learning dataset to determine a preliminary facial recognition value; and calculating the facial recognition confidence value based on the preliminary facial recognition value and a facial recognition weighted value. Further, determining the voice recognition confidence value comprises: inputting the audio file into the voice recognition machine learning dataset to determine a preliminary voice recognition value; and calculating the voice recognition confidence value based on the preliminary voice recognition value and a voice recognition weighted value.

In some instances, the processor-executable instructions, when executed, further facilitate: determining, based on sensor information from a wearable device, a preliminary sensor information value, wherein the preliminary sensor information value is associated with an oxygen level of the individual, a temperature reading of the individual, a pulse rate of the individual, or a humidity value associated with the individual; calculating a health characteristic confidence value based on the preliminary sensor information value and a health characteristic weighted value, and wherein determining whether the individual is sick is further based on the health characteristic confidence value.

In some examples, the processor-executable instructions, when executed, further facilitate: providing, to an enterprise computing system, a request for a plurality of weighted values associated with a particular type of illness; and receiving, from the enterprise computing system, the voice recognition weighted value associated with the particular type of illness, the health characteristic weighted value associated with the particular type of illness, and the facial recognition weighted value associated with the particular type of illness.

In some variations, the user device further comprises an image capturing device. The processor-executable instructions, when executed, further facilitate: using the image capturing device to obtain a second image of a portion of the individual's body, wherein the portion of the individual's body is any bodily portion of the individual other the individual's face, and wherein determining whether the individual is sick is further based on the second image of the portion of the individual's body.

In some instances, the prompt requests user feedback indicating whether to provide information to an enterprise computing system. The processor-executable instructions, when executed, further facilitate: based on the user feedback, providing information indicating the individual is sick to the enterprise computing system, wherein the information comprises geographical coordinates associated with the user device.

In another aspect, a system comprises a health characteristic device and a user device. The health characteristic device comprises one or more first processors; and a first non-transitory computer-readable medium having first processor-executable instructions stored thereon, wherein the first processor-executable instructions, when executed, facilitate: obtaining current sensor information indicating current health characteristics associated with an individual; and providing the current sensor information to a user device. The user device comprises one or more second processors; and a second non-transitory computer-readable medium having second processor-executable instructions stored thereon, wherein the second processor-executable instructions, when executed, facilitate: obtaining a facial image of the individual; obtaining an audio file comprising a voice recording of the individual; determining a facial recognition confidence value associated with whether the individual is sick based on inputting the facial image into a facial recognition machine learning dataset that is individualized for the individual; determining a voice recognition confidence value associated with whether the individual is sick based on inputting the audio file into a voice recognition machine learning dataset that is individualized for the individual; determining whether the individual is sick based on the facial recognition confidence value, the voice recognition confidence value, and the current sensor information from the health characteristic device; and causing display of a prompt indicating whether the individual is sick.

Examples may include one of the following features, or any combination thereof. For instance, in some examples, the first processor-executable instructions, when executed, further facilitate: obtaining first sensor information indicating first health characteristics associated with the individual; and providing the first sensor information to the user device. The second processor-executable instructions, when executed, further facilitate: generating a baseline health model of the individual based on the first sensor information, wherein determining whether the individual is sick is further based on comparing the current sensor information with the baseline health model.

In some instances, the first and current sensor information comprises one or more of an oxygen level of the individual, a temperature reading of the individual, a pulse rate of the individual, and a humidity value associated with the individual.

In some variations, the first processor-executable instructions, when executed, further facilitate: obtaining third sensor information indicating third health characteristics associated with the individual; and providing the third sensor information to the user device, and wherein the second processor-executable instructions, when executed, further facilitate: updating the baseline health model of the individual based on the third sensor information, wherein determining whether the individual is sick is further based on comparing the current sensor information with the updated baseline health model.

In yet another aspect, a method comprises: obtaining a facial image of an individual; obtaining an audio file comprising a voice recording of the individual; determining a facial recognition confidence value associated with whether the individual is sick based on inputting the facial image into a facial recognition machine learning dataset that is individualized for the individual; determining a voice recognition confidence value associated with whether the individual is sick based on inputting the audio file into a voice recognition machine learning dataset that is individualized for the individual; determining whether the individual is sick based on the facial recognition confidence value and the voice recognition confidence value; and causing display of a prompt indicating whether the individual is sick.

Examples may include one of the following features, or any combination thereof. For instance, in some examples, the method further comprises: obtaining training data comprising a plurality of facial images of the individual; and individualizing the facial recognition machine learning dataset for the individual based on training the facial recognition machine learning dataset using the plurality of facial images of the individual.

In some instances, the method further comprises: obtaining training data comprising a plurality of voice recordings of the individual; and individualizing the voice recognition machine learning dataset for the individual based on training the voice recognition machine learning dataset using the plurality of voice recordings of the individual.

In some variations, determining the facial recognition confidence value comprises: inputting the facial image into the facial recognition machine learning dataset to determine a preliminary facial recognition value; and calculating the facial recognition confidence value based on the preliminary facial recognition value and a facial recognition weighted value. Determining the voice recognition confidence value comprises: inputting the audio file into the voice recognition machine learning dataset to determine a preliminary voice recognition value; and calculating the voice recognition confidence value based on the preliminary voice recognition value and a voice recognition weighted value.

All examples and features mentioned above may be combined in any technically possible way.

BRIEF DESCRIPTION OF THE DRAWINGS

The subject technology will be described in even greater detail below based on the exemplary figures, but is not limited to the examples. All features described and/or illustrated herein can be used alone or combined in different combinations. The features and advantages of various examples will become apparent by reading the following detailed description with reference to the attached drawings which illustrate the following.

DETAILED DESCRIPTION

Examples of the presented application will now be described more fully hereinafter with reference to the accompanying FIGs., in which some, but not all, examples of the application are shown. Indeed, the application may be exemplified in different forms and should not be construed as limited to the examples set forth herein; rather, these examples are provided so that the application will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

Figure 1:
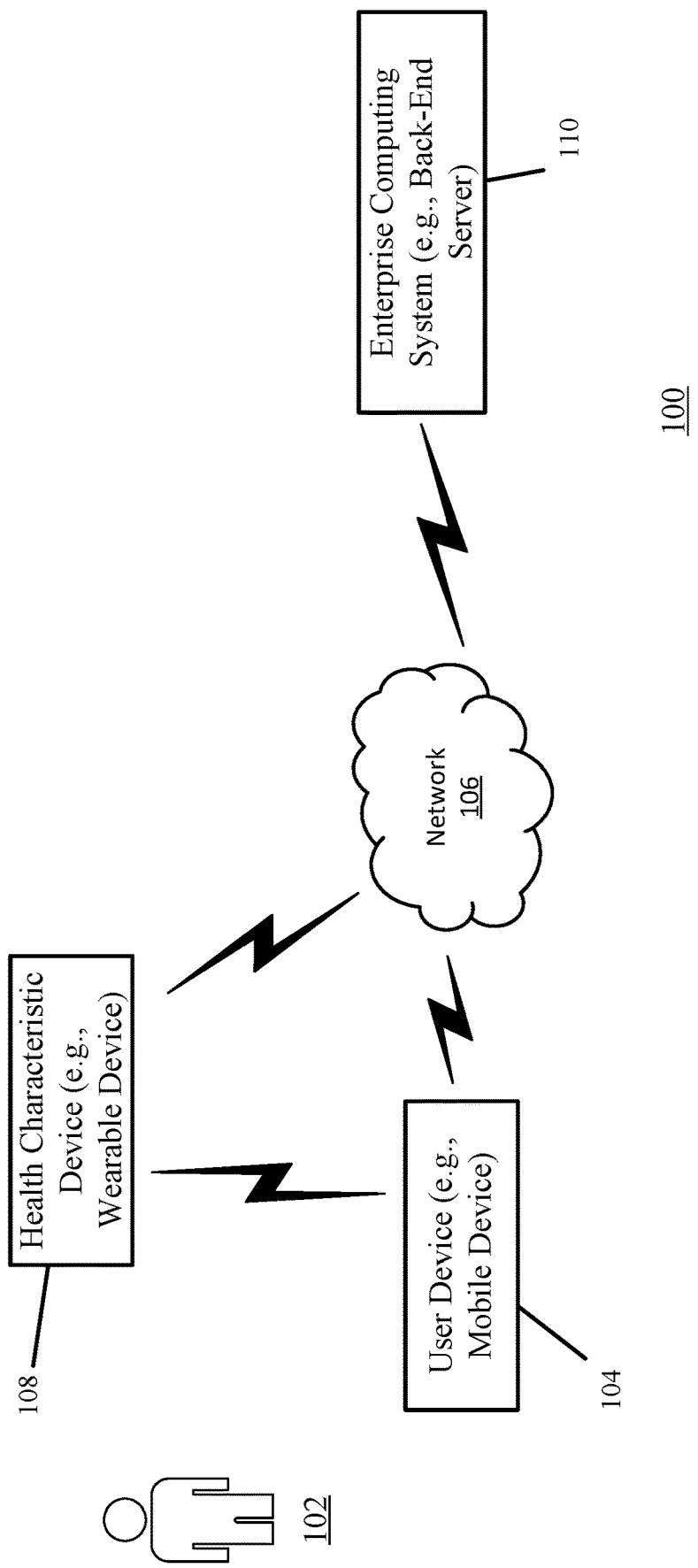
FIG. 1 is a simplified block diagram depicting an exemplary computing environment in accordance with one or more examples of the present application.

Systems, methods, and computer program products are herein disclosed that provide for using machine learning datasets to determine whether an individual is sick. FIG. 1 is a simplified block diagram depicting an exemplary environment in accordance with an example of the present application. The environment 100 includes an individual (e.g., user) 102, a user device (e.g., mobile device) 104 associated with the individual 102, a health characteristic device (e.g., wearable device) 108, and an enterprise computing system (e.g., back-end server) 110. Although the entities within environment 100 may be described below and/or depicted in the FIGs. as being singular entities, it will be appreciated that the entities and functionalities discussed herein may be implemented by and/or include one or more entities.

The entities within the environment 100 such as the user device 104, the health characteristic device (e.g., wearable device) 108, and the enterprise computing system (e.g., back-end server) 110 may be in communication with other systems within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100. Additionally, and/or alternatively, the user device 104 may be in communication with the health characteristic device 108 without using the network 106. For instance, the user device 104 may use one or more communication protocols such as WI-FI or BLUETOOTH to communicate with the health characteristic device 108.

Individual 102 may operate, own, and/or otherwise be associated with a user device 104. For instance, the user device 104 may be a mobile phone such as a smartphone that is owned and/or operated by the individual 102. The individual 102 may provide information to the other entities of environment 100 such as the enterprise computing system 110 using the user device 104. For example, the user device 104 may receive user input from the individual 102 such as indications to download, operate, and/or manage a software application associated with an enterprise organization. The enterprise organization may be any type of corporation, company, organization, and/or other institution. The software application may be an application that is used by the user device 104 to communicate with the health characteristic device 108 as well as the enterprise computing system 110. For example, the health characteristic device 108 may communicate with and/or provide information to the user device 104 such as sensor information associated with characteristics of the individual 102. Based on the sensor information, the user device 104 may determine whether the individual 102 is sick.

The user device 104 may be and/or include, but is not limited to, a desktop, laptop, tablet, mobile device (e.g., smartphone device, or other mobile device), smart watch, an internet of things (IOT) device, or any other type of computing device that generally comprises one or more communication components, one or more processing components, and one or more memory components. The user device 104 may be able to execute software applications managed by, in communication with, and/or otherwise associated with the enterprise organization.

The user device 104 may determine whether the individual 102 is sick using one or more machine learning/artificial intelligence datasets. For example, the user device 104 may receive a plurality of images (e.g., facial images) and/or voice recordings of the individual 102. The user device 104 may train one or more machine learning datasets using the images and voice recordings. For example, the user device 104 may input the images into a first machine learning dataset to train the first machine learning dataset and input the voice recordings into a second machine learning dataset to train the second machine learning dataset. Then, after the training has been completed, the user device 104 may use the trained machine learning datasets to determine whether the individual 102 is sick. For example, the user device 104 may receive a new image and voice recording of the individual 102. Then, the user device 104 may input the new image and voice recording into the trained machine learning datasets to determine whether the individual 102 is sick.

The health characteristic device 108 may be any device that is capable of detecting sensor information associated with the individual 102 and providing the sensor information to the user device 104. For example, the health characteristic device 108 may include one or more sensors such as an oxygen sensor, a temperature sensor, a pulse sensor, and/or a humidity sensor. The sensors may obtain/detect sensor information such as an oxygen level of the individual 102, a temperature of the individual 102, a pulse/heart rate of the individual 102, and/or a humidity of the individual 102. In some instances, the user device 104 may use the sensor information from the health characteristic device 108 as well as the trained machine learning datasets to determine whether the individual 102 is sick. For example, the user device 104 may determine one or more confidence values using the sensor information and/or the trained machine learning datasets. Afterwards, the user device 104 may use the confidence values to determine whether the individual 102 is sick. This will be described in further detail below.

In some instances, the health characteristic device 108 may be operatively coupled to or located on the individual's body. For instance, the health characteristic device 108 may be a wearable device such as a watch, bracelet, necklace, finger heart rate monitor, and so on. For example, the health characteristic device 108 may be a finger heart rate monitor or a bracelet that is capable of obtaining a heart rate and/or an oxygen level. The individual 102 may swipe the finger heart rate monitor or bracelet over their own forehead to determine the humidity and body temperature. Additionally, and/or alternatively, the health characteristic device 108 may be an IoT device.

The enterprise computing system 110 is a computing system that is associated with the enterprise organization. The enterprise computing system 110 includes one or more computing devices, computing platforms, systems, servers, and/or other apparatuses capable of performing tasks, functions, and/or other actions for the enterprise organization. In some instances, the enterprise computing system 110 may, for example, receive information from and/or provide information to the user device 104 and/or the health characteristic device 108. For instance, the enterprise computing system 110 may receive information indicating whether the individual 102 is sick. Based on this received information, the enterprise computing system 110 may provide a notification or alert indicating the individual 102 is sick.

The enterprise computing system 110 may be implemented using one or more computing platforms, devices, servers, and/or apparatuses. In some variations, the enterprise computing system 110 may be implemented as engines, software functions, and/or applications. In other words, the functionalities of the enterprise computing system 110 may be implemented as software instructions stored in storage (e.g., memory) and executed by one or more processors.

It will be appreciated that the exemplary environment depicted in FIG. 1 is merely an example, and that the principles discussed herein may also be applicable to other situations—for example, including other types of institutions, organizations, devices, systems, and network configurations. As will be described herein, the environment 100 may be used by health care enterprise organizations. However, in other instances, the environment 100 may be used by other types of enterprise organizations such as financial institutions or insurance institutions.

Figure 2:
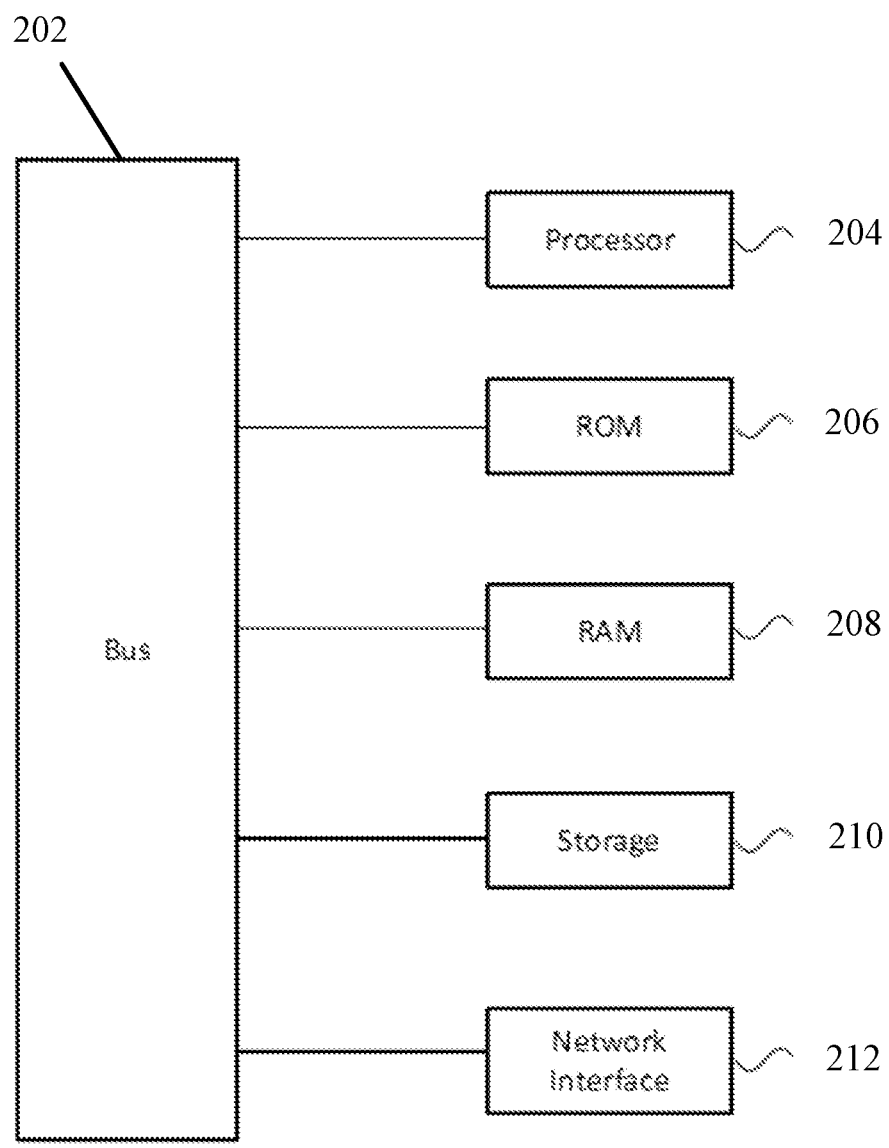
FIG. 2 is a simplified block diagram of one or more devices or systems within the exemplary environment of FIG. 1.

FIG. 2 is a block diagram of an exemplary system and/or device 200 (e.g., the user device 104, the health characteristic device 108, and/or the enterprise computing system 110) within the environment 100. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 are merely exemplary and might not be inclusive of every component, server, device, computing platform, and/or computing apparatus within the device/system 200. For example, as will be described below, the health characteristic device 108 may include some of the components within the device/system 200 and may also include further components such as one or more sensors. Additionally, and/or alternatively, the device/system 200 may further include components that might not be included within every entity of environment 100.

Figure 3:
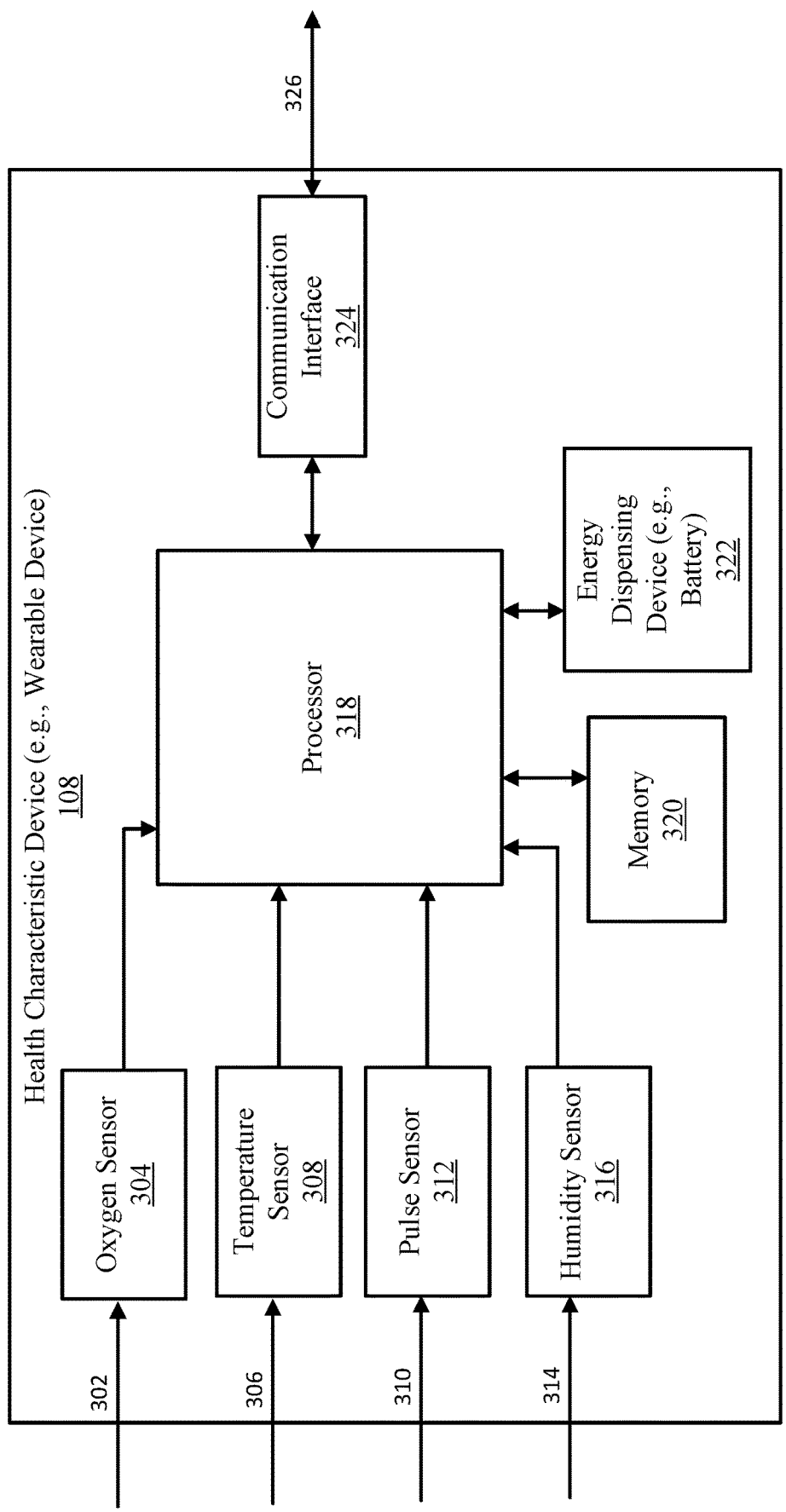
FIG. 3 is another simplified block diagram depicting a health characteristic device in accordance with one or more examples of the present application.

FIG. 3 is a simplified block diagram depicting a health characteristic device 108 in accordance with one or more examples of the present application. In some examples, the health characteristic device 108 may be a wearable device such as a device that is capable of being worn on and/or operatively coupled to the individual 102 (e.g., a smart watch or bracelet). The health characteristic device 108 may be used to obtain health characteristics such as a pulse rate, oxygen level, humidity, and/or body temperature of the individual 102.

The health characteristic device 108 includes multiple components such as an oxygen sensor 304, a temperature sensor 308, a pulse sensor 312, a humidity sensor 316, processor(s) 318, memory 320, an energy dispensing device 322 (e.g., battery), and/or a communication interface 324. The oxygen sensor 304 receives information 302 indicating an oxygen level ($O_2$ level) of the individual 102. The oxygen level may be the amount of oxygen that is within the individual's 102 blood stream. The oxygen sensor 304 may be any type of sensor that is capable of detecting an oxygen level of the individual 102 and may be/include a MAX30102 heart rate sensor, a pulse oximeter sensor, and/or another type of oxygen sensor. The oxygen sensor 304 may detect the oxygen information that includes the oxygen level of the individual 102 and provide the oxygen information to the processor 318. For example, the oxygen sensor 304 may use a light emitting diode (LED) such as a red LED or infrared LED and/or a photodetector to determine the blood oxygen content and heart rate of the individual 102.

The temperature sensor 308 receives information 306 indicating a temperature associated with the individual 102 such as a body temperature of the individual 102. The temperature sensor 308 may be any type of sensor that is capable of detecting the body temperature of the individual 102 and may be/include one or more infrared (IR) temperature sensors, thermistors, thermal cameras, resistance temperature detectors (RTDs), and/or other types of temperature sensors. For instance, the temperature sensor 308 may detect temperature information that includes the body temperature of the individual 102 and provide the temperature information to the processor 318. In some instances, the temperature sensor 308 may be and/or include the ADAFRUIT AMG8833 IR thermal camera breakout and/or the ADAFRUIT Si7021 temperature & humidity sensor breakout board.

The pulse sensor 312 receives information 310 indicating a pulse rate or heart rate associated with the individual 102. The pulse sensor 312 may be any type of sensor that is capable of detecting the pulse/heart rate of the individual 102. For instance, the pulse sensor 312 may detect pulse information that includes the pulse/heart rate of the individual 102 and provide the pulse information to the processor 318.

The humidity sensor 316 receives information 314 indicating a humidity/moisture associated with the individual 102. The humidity sensor 316 may detect and measure water vapor including the humidity/moisture of the region on the individual's 102 body that the health characteristic device 108 is located. For example, if an individual 102 is sick, the individual 102 may begin perspiring or sweating. The humidity sensor 316 may detect the water vapor content on the skin of the individual 102 and/or the area surrounding the humidity sensor 316. The humidity sensor 316 may provide the humidity information that includes the water vapor content of the individual 102 to the processor 318.

While only the oxygen sensor 304, the temperature sensor 308, the pulse sensor 312, and the humidity sensor 316 are shown in FIG. 3, in some examples, the health characteristic device 108 may include additional and/or alternative sensors.

The processor 318 may be any type of hardware and/or software logic, such as a central processing unit (CPU), RASPBERRY PI processor/logic, controller, and/or logic, that executes computer executable instructions for performing the functions, processes, and/or methods described herein. For example, the processor 318 may receive oxygen, temperature, pulse, and humidity information from the sensors 304, 308, 312, and 316. Afterwards, the processor 318 may provide this information to another device such as the user device 104.

The health characteristic device 108 includes memory 320. In some examples, the memory 320 may be and/or include a computer-usable or computer-readable medium such as, but not limited to, an electronic, magnetic, optical, electromagnetic, infrared, or semiconductor computer-readable medium. More specific examples (e.g., a non-exhaustive list) of the computer-readable medium may include the following: an electrical connection having one or more wires; a tangible medium such as a portable computer diskette, a hard disk, a time-dependent access memory (RAM such as the RAM 208), a ROM such as ROM 206, an erasable programmable read-only memory (EPROM or Flash memory), a compact disc read-only memory (CD_ROM), or other tangible optical or magnetic storage device. The computer-readable medium may store computer-readable instructions/program code for carrying out operations of the present application. For example, when executed by the processor 318, the computer-readable instructions/program code may carry out operations described herein.

The health characteristic device 108 includes a communication (e.g., network) interface 324. The processor 318 uses the communication interface 324 to communicate with other devices and/or systems within the environment 100. The communication interface 324 may include the functionalities and/or be the network interface 212 shown in FIG. 2. For example, the fall detection processor(s) 306 may receive and/or provide sensor information 326 to the user device 104 using the communication interface 324. The sensor information 326 may include the oxygen, temperature, pulse, and humidity information from the sensors 304, 308, 312, and 316.

Figure 4:
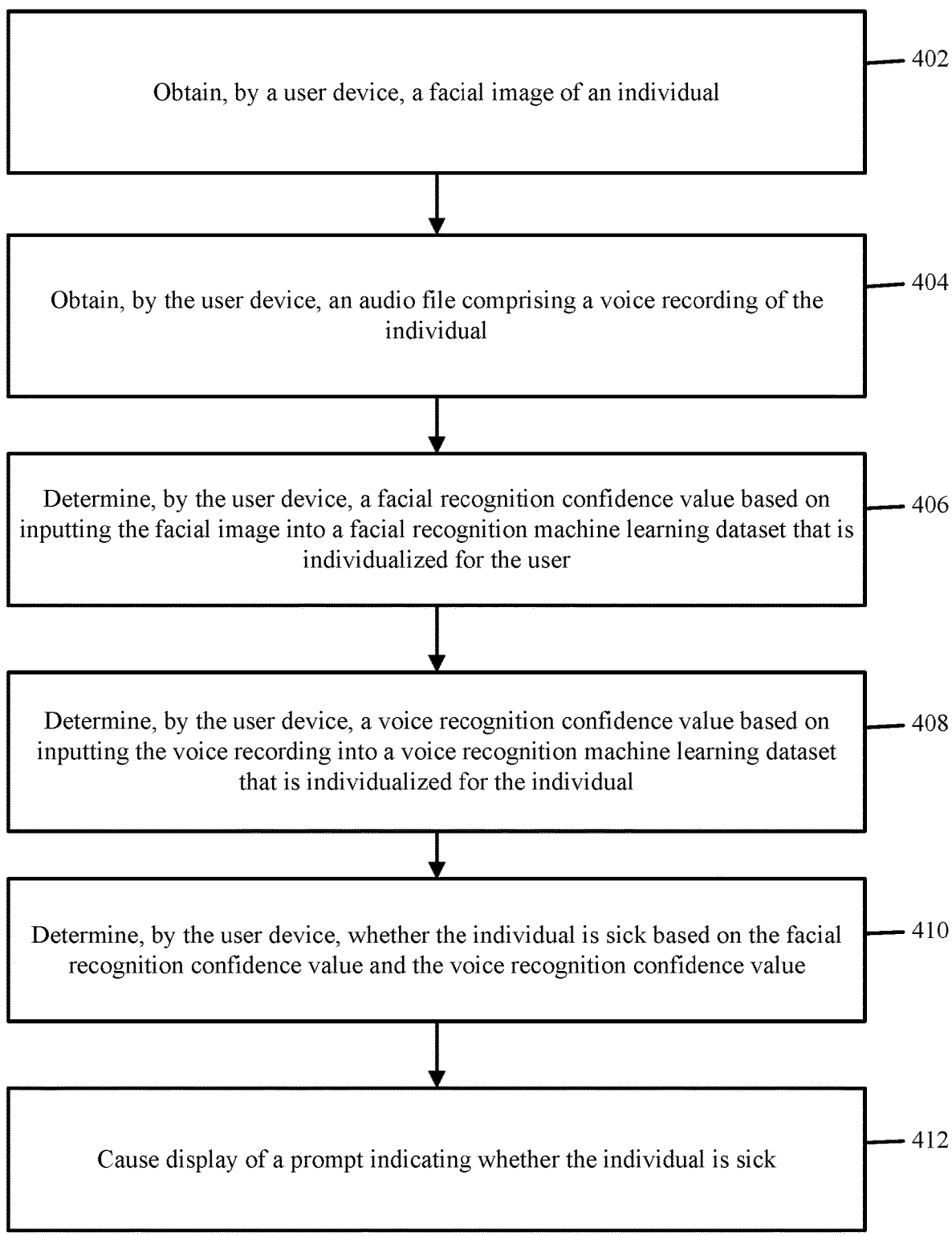
FIG. 4 is an exemplary process for using machine learning datasets to determine whether an individual is sick in accordance with one or more examples of the present application.

FIG. 4 is an exemplary process 400 for operating one or more devices to determine whether an individual 102 is sick in accordance with one or more examples of the present application. The process 400 may be performed by the user device 104 of environment 100 shown in FIG. 1. However, it will be recognized that the process 400 may be performed in any suitable environment and that any of the following blocks may be performed in any suitable order. The descriptions, illustrations, and processes of FIG. 4 are merely exemplary and the process 400 and/or the user device 104 may use other descriptions, illustrations, and processes for determining whether an individual 102 is sick or unwell.

At block 402, a user device (e.g., the user device 104) obtains a facial image of an individual 102. The facial image may be an image of at least a portion of the individual's face (e.g., eyes, nose, ears, mouth, cheeks, jaw) and/or regions around the individual's face (e.g., neck or hair). For example, the user device 104 may include an image capturing device (e.g., a camera) and may use the image capturing device to capture an image of the face of the individual 102. The facial image may indicate whether the individual 102 is sick or unwell.

For example, in some instances, an individual 102 may wake up in the morning and feel unwell, but they may be unsure as to whether they are actually sick (e.g., have a virus or disease that may be transmittable to others within a workplace), have allergies, or other conditions. Accordingly, the individual 102 may use the user device 104 to determine whether they are sick and should stay home. For instance, as will be explained below, the user device 104 may use the facial image, a voice recording of the individual 102, and/or sensor information from the health characteristic device 108 to determine whether the individual 102 is sick.

In some examples, the user device 104 may capture an image or video of the individual 102. In other examples, the user device 104 may use the image capturing device to stream a real-time image of the individual 102 on a display screen of the user device 104. For instance, the user device 104 may continuously capture and display real-time images of the individual 102. In some variations, the user device 104 may provide feedback to the individual 102 based on the continuously captured/displayed individual 102. For example, the real-time images may only show a portion of the individual's 102 face such as the left side of the face. The user device 104 may provide feedback (e.g., display a prompt) indicating for the individual 102 to re-arrange themselves such that the entire face is able to be captured by the user device 104.

At block 404, the user device 104 obtains an audio file comprising a voice recording of the individual 102. The voice recording may be and/or include a phrase or sentence uttered by the individual 102. For example, the user device 104 may include a microphone and/or other types of audio devices that may convert sounds into electrical signals (i.e., audio signals). The individual 102 may utter a phrase (e.g., "Mary had a little lamb") and the user device 104 may capture the utterance as an audio file.

In some examples, the user device 104 may capture the image and voice recording of the individual 102 based on executing a software application associated with an enterprise application. For example, the user device 104 may download/install the software application. Afterwards, the software application may prompt (e.g., display a prompt) the individual 102 to provide an image of the individual's face and utter a phrase.

At block 406, the user device 104 determines a facial recognition confidence value based on inputting the facial image into a facial recognition machine learning dataset that is individualized for the individual 102.

The facial recognition machine learning dataset may a machine learning/artificial intelligence algorithm, model, and/or dataset. The facial recognition machine learning dataset may be trained using facial images of the individual 102 so that it is able to better determine whether the individual 102 is sick. For example, prior to performing process 400, the user device 104 may receive a generic facial recognition machine learning dataset from a second device such as the enterprise computing system 110. The generic facial recognition machine learning dataset may be an untrained machine learning dataset and/or a machine learning dataset that has been trained using facial images from a plurality of individuals. The user device 104 may capture numerous (e.g., fifty) facial images of the individual 102 and train the facial recognition machine learning dataset using the captured images. For example, the user device 104 may capture images of the individual 102 when the individual 102 is healthy. Then, the user device 104 may train a facial recognition machine learning dataset using the images of when the individual 102 is healthy such that the facial recognition machine learning dataset is capable of predicting whether the individual 102 is sick. After training the facial recognition machine learning dataset, the user device 104 may obtain a facial image of the individual 102 at block 402. At block 406, the user device 104 may input the facial image into the trained facial recognition machine learning dataset to determine whether the individual 102 is sick.

In other words, when a person is sick, the person's face may have certain features that are different from the baseline (e.g., when the person is healthy). For example, when an individual 102 is sick, they have a discoloration of the eyes (e.g., the eyes may be watery), discoloration or reflectiveness in skin color (e.g., the skin tone of the individual 102 may be altered), dryness of the lips (e.g., cracked lips), discoloration of the nose (e.g., red nose that may indicate the individual 102 has been rubbing it), flushed cheeks, and so on. Accordingly, by using images of the individual 102 when healthy to train the facial recognition machine learning dataset, the user device 104 may individualize the facial recognition machine learning dataset. For example, each person's skin tone may be of a different color or their flushed cheeks may turn different colors. For instance, the discoloration of an African American person's skin may change differently when they are sick as compared to an Asian American or a Caucasian. Therefore, by using the images of the individual 102 to determine whether the individual 102 is sick, the facial recognition machine learning dataset may be better able to predict when the individual 102 is actually sick (e.g., by comparing the pixels/pixel colors of the captured images when the individual 102 is healthy and the pixels/pixel colors of the image captured at block 402).

In some variations, the user device 104 may train the facial recognition machine learning dataset using images taken of the individual 102 when the individual 102 is actually sick. In some examples, the user device 104 may train the facial recognition machine learning dataset using images of the individual 102 that have been altered such that the individual 102 appears to be sick. For example, the user device 104 may capture images of the individual 102 when the individual 102 is healthy. Then, the user device 104 may alter the image such that the individual 102 appears to be sick (e.g., alter the image such that the individual 102 appears to be flushed, sweaty, pale, have watery eyes, and/or have a red nose). The user device 104 may train the facial recognition machine learning dataset using the altered images of the individual 102. In some instances, the user device 104 may alter the images of the individual 102 by using or applying one or more filters.

After inputting the facial image from block 402 into the facial recognition machine learning dataset, the user device 104 may determine a facial recognition confidence value. The facial recognition confidence value may be a number, rating, weighted value, percentage or other identifier that is associated with the facial recognition machine learning dataset. For instance, in some variations, the output from the facial recognition machine learning dataset may be a percentage (e.g., 80%) indicating whether the individual 102 is sick. As will be explained below, the user device 104 may use this percentage along with a voice recognition confidence value and/or additional confidence values (e.g., health characteristic confidence values) to determine whether the individual 102 is actually sick.

In some instances, a server (e.g., the enterprise computing system 110) may perform the training of the facial recognition machine learning dataset. For example, the user device 104 may capture a plurality of facial images (e.g., fifty images) of the individual 102 and send the plurality of facial images to the enterprise computing system 110. The enterprise computing system 110 may train the facial recognition machine learning dataset using the received images and provide the trained facial recognition machine learning dataset back to the user device 104 and/or another device.

In some examples, the enterprise computing system 110 and/or the user device 104 may train the facial recognition machine learning dataset using TENS ORFLOW, HAAR CASCADE, and/or other machine learning algorithms (e.g., supervised, unsupervised, and/or deep learning artificial intelligence algorithms).

At block 408, the user device 104 determines a voice recognition confidence value based on inputting the voice recording into a voice recognition machine learning dataset that is individualized for the individual 102.

The voice recognition machine learning dataset may a machine learning/artificial intelligence algorithm, model, and/or dataset. The voice recognition machine learning dataset may be trained using voice recordings of the individual 102 so that it is able to better determine whether the individual 102 is sick. For example, prior to performing process 400, the user device 104 may receive a generic voice recognition machine learning dataset from a second device such as the enterprise computing system 110. The generic voice recognition machine learning dataset may be an untrained machine learning dataset and/or a machine learning dataset that has been trained using voice recognition from a plurality of individuals. The user device 104 may record numerous voice recordings of the individual 102 uttering one or more phrases (e.g., "Mary had a little lamb"). In some instances, the recordings may be the individual 102 uttering the same phrase. Then, the user device 104 may train the voice recognition machine learning dataset using the voice recordings. For example, the user device 104 may record the voice recordings of the individual 102 when the individual 102 is healthy. Then, the user device 104 may train a voice recognition machine learning dataset using the voice recordings of when the individual 102 is healthy such that the voice recognition machine learning dataset is capable of predicting whether the individual 102 is sick. After training the voice recognition machine learning dataset, the user device 104 may obtain a voice recognition of the individual 102 at block 402. At block 408, the user device 104 may input the voice recognition into the trained voice recognition machine learning dataset to determine whether the individual 102 is sick.

In other words, when a person is sick, the person's voice may change as compared to the baseline (e.g., when the person is healthy). For example, when an individual 102 is sick, the frequency, amplitude of voice, tone, volume, cadence, rhythm of voice, and/or other features may change such as the individual's 102 voice may become raspy when they are sick. Accordingly, by using voice recordings of the individual 102 when healthy to train the vocal recognition machine learning dataset, the user device 104 may individualize the voice recognition machine learning dataset. For example, each person's voice is different and people's voices may change differently when they are sick. Therefore, by using the voice recordings of the individual 102 to determine whether the individual 102 is sick, the vocal recognition machine learning dataset may be better able to predict when the individual 102 is actually sick (e.g., by comparing the bit patterns within the voice recordings used to train the dataset and the bit patterns of the voice recording from block 404).

In some variations, the user device 104 may train the voice recognition machine learning dataset using voice recordings taken of the individual 102 when the individual 102 is actually sick. In some examples, the user device 104 may train the voice recognition machine learning dataset using voice recordings that have been altered such that it appears the individual 102 is sick. For example, the user device 104 may record voice recordings of the individual 102 when the individual 102 is healthy. Then, the user device 104 may alter the voice recordings such that the individual 102 appears to be sick (e.g., change the input sound files of the individual 102 using an audio synthesizer). For instance, the sound waves of the voice recording may be described using characteristics such as wavelength, amplitude, time-period, frequency, and/or velocity/speed. The user device 104 may use or apply different filters based on these five characteristics to make it appear the individual 102 is sick. For example, the altered voice recording may change the individual's 102 voice to appear to be hoarse, muffled, or even insert pauses as if the individual 102 is catching their breath while speaking. The altered voice recording may further simulate wheezing or coughing.

After inputting the voice recording from block 404 into the voice recognition machine learning dataset, the user device 104 may determine a voice recognition confidence value. The voice recognition confidence value may be a number, rating, weighted value, percentage or other identifier that is associated with the voice recognition machine learning dataset. For instance, in some variations, the output from the voice recognition machine learning dataset may be a percentage (e.g., 90%) indicating whether the individual 102 is sick.

In some instances, a server (e.g., the enterprise computing system 110) may perform the training of the voice recognition machine learning dataset. For example, the user device 104 may capture a plurality of voice recordings of the individual 102 and send the plurality of voice recordings to the enterprise computing system 110. The enterprise computing system 110 may train the voice recognition machine learning dataset using the received voice recordings and provide the trained voice recognition machine learning dataset back to the user device 104 and/or another device.

In some examples, the enterprise computing system 110 and/or the user device 104 may train the voice recognition machine learning dataset using TENSORFLOW and/or other machine learning algorithms (e.g., supervised, unsupervised, and/or deep learning artificial intelligence algorithms).

At block 410, the user device 104 determines whether the individual 102 is sick based on the facial recognition confidence value and the voice recognition confidence value. For example, after determining the facial recognition confidence value based on the facial recognition machine learning dataset at block 406 and determining the voice recognition confidence value based on the voice recognition machine learning dataset at block 408, the user device 104 may use these two values to determine whether the individual is sick.

For instance, in some examples, the facial recognition confidence value and the voice recognition confidence value may be numerical values and/or percentages. The user device 104 may use weighted values for the facial and voice recognition confidence values to determine whether the individual 102 is sick. For example, the user device 104 may weigh the facial and voice recognition confidence values the same and determine a combined value (e.g., the user device 104 may determine an average of the facial and voice recognition confidence values ((95%+91%)/2=93%). Based on the combined value (93%) being above a threshold (e.g., 90%), then the user device 104 may determine the individual 102 is sick. In other examples, the user device 104 may weigh the facial and voice recognition confidence values differently to determine an output. For instance, the facial recognition confidence value may be more accurate in determining whether the individual 102 is sick as compared to the voice recognition confidence value. Accordingly, the user device 104 may use a weighted 80/20 split between the facial to voice recognition confidence value to determine whether the individual 102 is sick. For example, if the facial recognition confidence value is 95% and the voice recognition confidence value is 80%, then the combination of these two values using the weighted split may be 92% (e.g., 95*0.8+80*0.2=92). Based on the combined value (92%) being above a threshold (e.g., 90%), then the user device 104 may determine the individual 102 is sick.

In some variations, the weighted values for the facial/voice recognition confidence values and/or the threshold that are used to determine whether the individual 102 is sick may be based on the type of illness or disease. For example, for a common cold, the weighted value for the facial recognition confidence value may be 80%, the weighted value for the voice recognition confidence value may be 50%, and the threshold used to determine whether the individual 102 is sick may be 90%. For the flu, the weighted value for the facial recognition confidence value may be 60%, the weighted value for the voice recognition confidence value may be 40%, and the threshold used to determine whether the individual 102 is sick may be 90%. In other words, in addition to the software application executing on the user device 104 requesting a facial image and a voice recording from the individual 102 at blocks 402 and 404, the user device 104 may further request user input indicating a particular illness to test for (e.g., flu, common cold, pneumonia, coronavirus-19 (COVID 19), and so on).

In some instances, the user device 104 may receive the weighted values for the facial/voice recognition confidence values and/or the threshold from a second device such as the enterprise computing system 110. In other instances, the user device 104 may already store these values/threshold within the memory. Subsequently, the user device 104 may receive an update to one or more of these values/thresholds from the second device (e.g., change the threshold to determine whether the individual 102 is sick from 90% to 85%).

The weighted values and thresholds, including the values/thresholds for particular illnesses, are merely exemplary and the user device 104 may use additional and/or alternative weighted values and thresholds to determine whether the individual 102 is sick. Further, while the above describes using weighted values to determine whether the individual 102 is sick, in some instances, the user device 104 may use additional and/or alternative methods, mathematical equations/formulas, processes, and/or other algorithms to determine whether the individual 102 is sick. For instance, the user device 104 may use a ranking system to determine whether the individual 102 is sick. The ranking system may indicate a weighted value (e.g., 70%) for the first or primary ranked confidence value, a weighted value (e.g., 20%) for the secondary ranked confidence value, and/or one or more weighted value for tertiary ranked confidence values (e.g., the confidence values associated with the sensor information, which is described below).

At block 412, the user device 104 may cause display of a prompt indicating whether the individual 102 is sick. For instance, based on determining the individual 102 is sick using block 410 (e.g., comparing a combination of the facial/voice recognition confidence values with a threshold), the user device 104 may cause display of a prompt such as a text on a display screen of the user device 104 stating "You are sick, please stay home." In some examples, the user device 104 may determine the individual 102 is not sick. Therefore, the user device 104 may log this instance as a false positive and/or display a prompt indicating the individual 102 is not sick (e.g., the individual 102 is "safe to go to work").

In some instances, in addition to using the facial/voice recognition confidence values, the user device 104 may further use sensor information (e.g., oxygen level, temperature of the individual 102, pulse rate, and/or humidity of the individual 102) from the health characteristic device 108 to determine whether the individual 102 is sick. For example, the user device 104 and/or the health characteristic device 108 may store baseline values for the sensor information including the oxygen level, temperature, humidity, and pulse rate associated with the individual 102. For instance, the health characteristic device 108 may obtain the sensor information at a first instance in time when the individual 102 is healthy. Subsequently, the health characteristic device 108 may store the obtained sensor information as baseline sensor values in memory (e.g., memory 320). Additionally, and/or alternatively, the health characteristic device 108 may provide the obtained baseline sensor information to the user device 104 and the user device 104 may store this baseline sensor information in memory (e.g., storage 210). In some variations, the health characteristic device 108 and/or the user device 104 may generate a baseline health model of the individual 102. The baseline health model may include one or more sensor measurements such as an average pulse rate, humidity value, oxygen level, and/or body temperature of the individual 102 that is obtained over a period of time (e.g., several minutes, several days, and/or a longer period of time).

At a second instance in time such as when the user device 104 is performing process 400, the health characteristic device 108 may obtain new (i.e., current) sensor information including the oxygen level, temperature, humidity, and/or pulse rate associated with the individual 102. The health characteristic device 108 may provide the new sensor information to the user device 104. Based on comparing the new sensor information with the baseline sensor information (e.g., obtained when the individual 102 is healthy), the user device 104 may determine whether the individual 102 is sick. For instance, based on a difference (e.g., difference from a mean) between a sensor value (e.g., oxygen level) from the baseline sensor information and a sensor value (e.g., oxygen level) from the new sensor information, the user device 104 may determine a health characteristic confidence value (e.g., an oxygen level confidence value). The user device 104 may use the health characteristic confidence value along with the facial and/or voice recognition confidence values to determine whether the individual 102 is sick. In some instances, the user device 104 may use one health characteristic confidence value for the sensor information. In other instances, the user device 104 may use multiple health characteristic confidence values for the sensor information including a health characteristic confidence value for each type of sensor information (e.g., a temperature confidence value, an oxygen confidence value, a pulse rate confidence value, and/or a humidity confidence value).

In some examples, similar to the above, the user device 104 may use weighted values for the health characteristic confidence values to determine whether the individual 102 is sick. For instance, for the flu, the weighted value for the temperature confidence value may be 60%, the weighted value for the humidity confidence value may be 10%, the weighted value for the voice recognition confidence value may be 30%, and the threshold used to determine whether the individual 102 is sick (e.g., has the flu) may be 90%. In other words, in some examples, the user device 104 may determine whether the individual 102 is sick without using one or more of the voice/facial recognition confidence values. In other examples, for COVID 19, the weighted value for the temperature recognition confidence value may be 50%, the weighted value for the voice recognition confidence value may be 30%, the weighted value for the facial recognition confidence value may be 20%, and the threshold used to determine whether the individual 102 is sick (e.g., has COVID 19) may be 90%.

In some variations, similar to the weights for the facial/voice recognition confidence values, the user device 104 may receive the weighted values and/or updates to the weighted values from the second device such as the enterprise computing system 110.

In some instances, the user device 104 and/or the health characteristic device 108 may update the baseline sensor information prior to using the baseline sensor information to determine whether the individual 102 is sick. For example, the baseline sensor information may change due to various factors. For instance, if an individual 102 begins exercising more or as the individual gets older, the baseline sensor information (e.g., pulse rate or body temperature) may change for the individual 102 when they are healthy and may also change when they are sick. As such, the user device 104 and/or the health characteristic device 108 may update the baseline sensor information for the individual 102 to ensure it is sufficiently accurate to determine whether the individual 102 is sick. For example, the user device 104 and/or the health characteristic device 108 may update the baseline sensor information after a certain time elapsing (e.g., every year).

Additionally, and/or alternatively, the user device 104 and/or the health characteristic device 108 may update the baseline sensor information based on obtaining abnormal readings over a certain time period. For instance, if the baseline sensor information (e.g., pulse rate) exceeds (e.g., is above or below) a certain threshold for a certain time period (e.g., a week or a month), then the user device 104 and/or the health characteristic device 108 may update the baseline sensor information. For example, if the pulse rate is constantly above a certain threshold for a month or so, then the user device 104 and/or the health characteristic device 108 may update the baseline pulse rate. In some instances, the user device 104 and/or the health characteristic device 108 may update the baseline sensor information based on user feedback. For instance, if the baseline sensor information (e.g., pulse rate) is constantly above a certain threshold, then the user device 104 may display a prompt requesting user feedback as to whether the individual 102 would want to update the baseline sensor information. Based on the user feedback, the user device 104 may update the baseline sensor information.

In some instances, at block 412, the user device 104 may provide information indicating whether the individual 102 is sick to a second device such as the enterprise computing system 110. For example, after determining the individual is sick, the user device 104 may cause display of a prompt requesting user feedback as to whether to provide this determination to another device such as forwarding an email to the individual's boss or co-worker. Additionally, and/or alternatively, the user device 104 may display a prompt requesting user feedback as to whether to provide this determination to a doctor/physician or to set up a doctor appointment, clinical visit, minute clinic appointment, disease testing (e.g., COVID 19 testing), and so on.

In some examples, the enterprise computing system 110 may receive information from the user device 104. The information may indicate whether the individual 102 is sick as well as additional information. For example, the enterprise computing system 110 may receive location data (e.g., geographical location information) associated with the individual 102 and/or the user device 104. The enterprise computing system 110 may perform communication (e.g., trusted communication) with another device such as a device running an application programming interface (API). For instance, the enterprise computing system 110 may communicate with a doctor/physician's computing system/API to set up an appointment for the individual 102. Additionally, and/or alternatively, using the location data, the enterprise computing system 110 may determine whether the individual 102 has infected additional people and/or the enterprise computing system 110 may perform contact tracing. In other words, the enterprise computing system 110 may determine whether the individual 102 could possibly be patient zero as well as whether the individual 102 may have infected more people.

In some instances, the enterprise computing system 110 and/or the user device 104 may provide the information used to determine whether the individual 102 is sick to another device such as the doctor/clinic/physician's computing system/API. For example, the enterprise computing system 110 and/or the user device 104 may provide the baseline sensor information and/or the new sensor information (e.g., the sensor information such as the pulse rate that is used to determine whether the individual 102 is sick) to the other device. Additionally, and/or alternatively, the enterprise computing system 110 and/or the user device 104 may provide the facial image of the individual 102 and/or audio file that includes the voice recording of the individual 102 to the other device.

In some variations, at block 410, the user device 104 may further use another image of the individual 102 (e.g., an image of the individual's skin) to determine whether the individual 102 is sick. For instance, in addition to the facial image of the individual 102, the user device 104 may receive a second image of the individual 102 that is not a facial image. For example, the second image may be an image of the skin or a body part (e.g., forearm, torso, and so on) of the individual 102. The user device 104 may use a machine learning dataset (e.g., the facial recognition machine learning dataset or a new machine learning dataset that is specific to the portion of the individual 102 shown in the second image) to determine a second image confidence value. Then, the user device 104 may use the second image confidence value along with the facial/voice recognition confidence values and/or the health characteristic confidence values to determine whether the individual 102 is sick.

Figure 5:
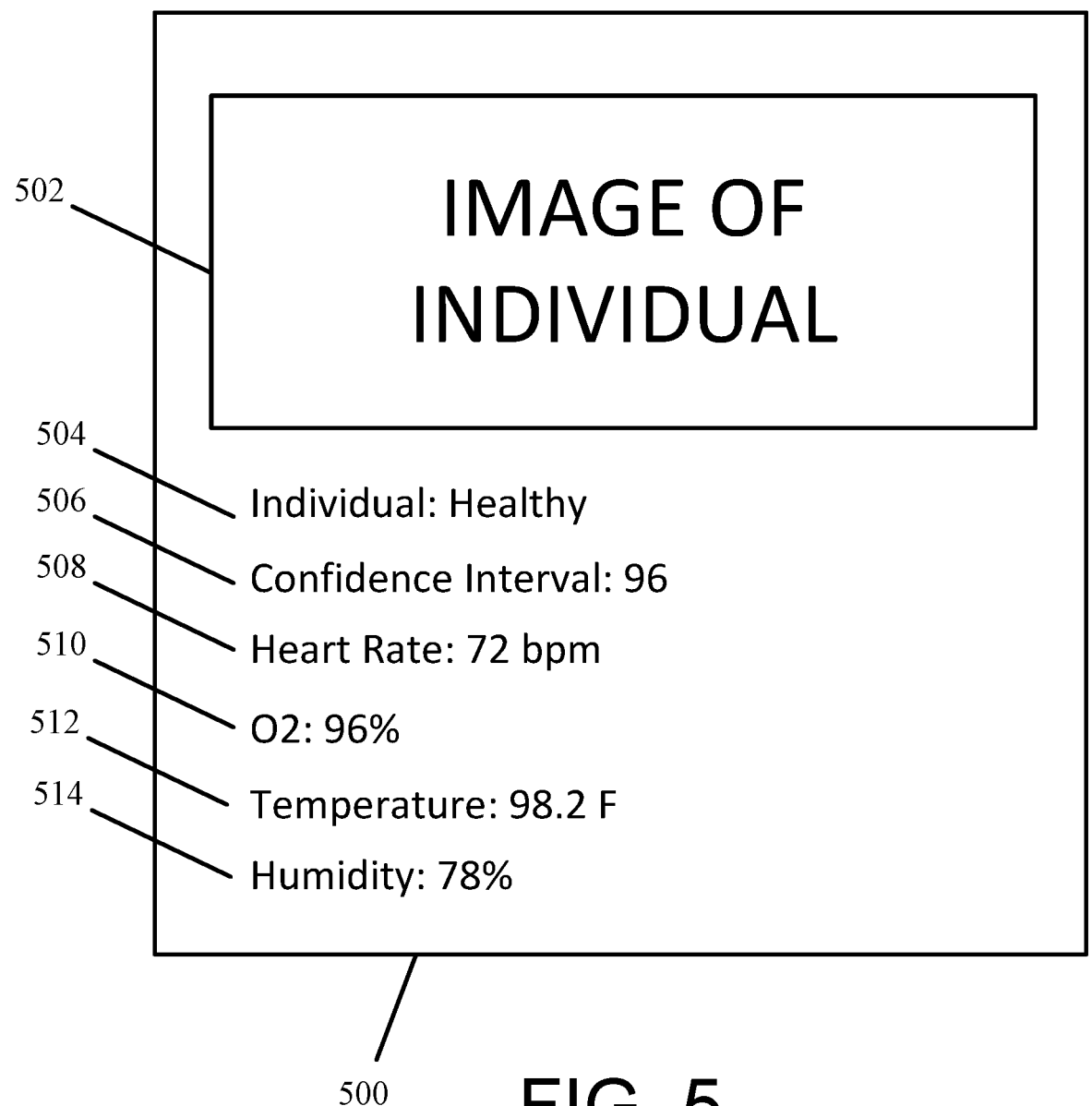
FIG. 5 is a display screen capable of being shown on a user device in accordance with one or more examples of the present application.

FIG. 5 shows a display screen 500 that the user device 104 may display to indicate whether the individual 102 is sick. The display screen 500 is merely exemplary and the user device 104 may display a different display screen indicating the prompt or notification. Referring to FIG. 5, the display screen 500 may include an image of the individual 102. The image may be a facial image of the individual 102 such as the facial image obtained at block 402. In some instances, as described above, the image may be real-time image of the individual 102. The display screen 500 may further include information 504-514. The information 504 includes a text prompt indicating whether the individual is healthy ("Individual: Healthy"), information 506 indicates a confidence interval (value) describing an accuracy of the determination of whether the individual 102 is healthy ("Confidence Interval: 96"), and information 508-514 indicates health characteristics such as the heart rate, oxygen level, temperature, and humidity from the health characteristic device 108 (e.g., "Heart Rate: 72 bpm", "O2: 96%", "Temperature: 98.2 F", "Humidity 78%"). In some instances, while not shown in FIG. 5, the display screen of the user device 104 may display a face analysis using the facial image (e.g., the facial recognition confidence value) and a voice analysis using the voice recording (e.g., the voice recognition confidence value). In other instances, if facial image/voice recording is suspected to not be of the individual 102 (e.g., the facial image/voice recording is associated with another individual), the user device 104 may cause display of a prompt indicating/requesting whether the facial image/voice recording is of another individual.

Figure 6:
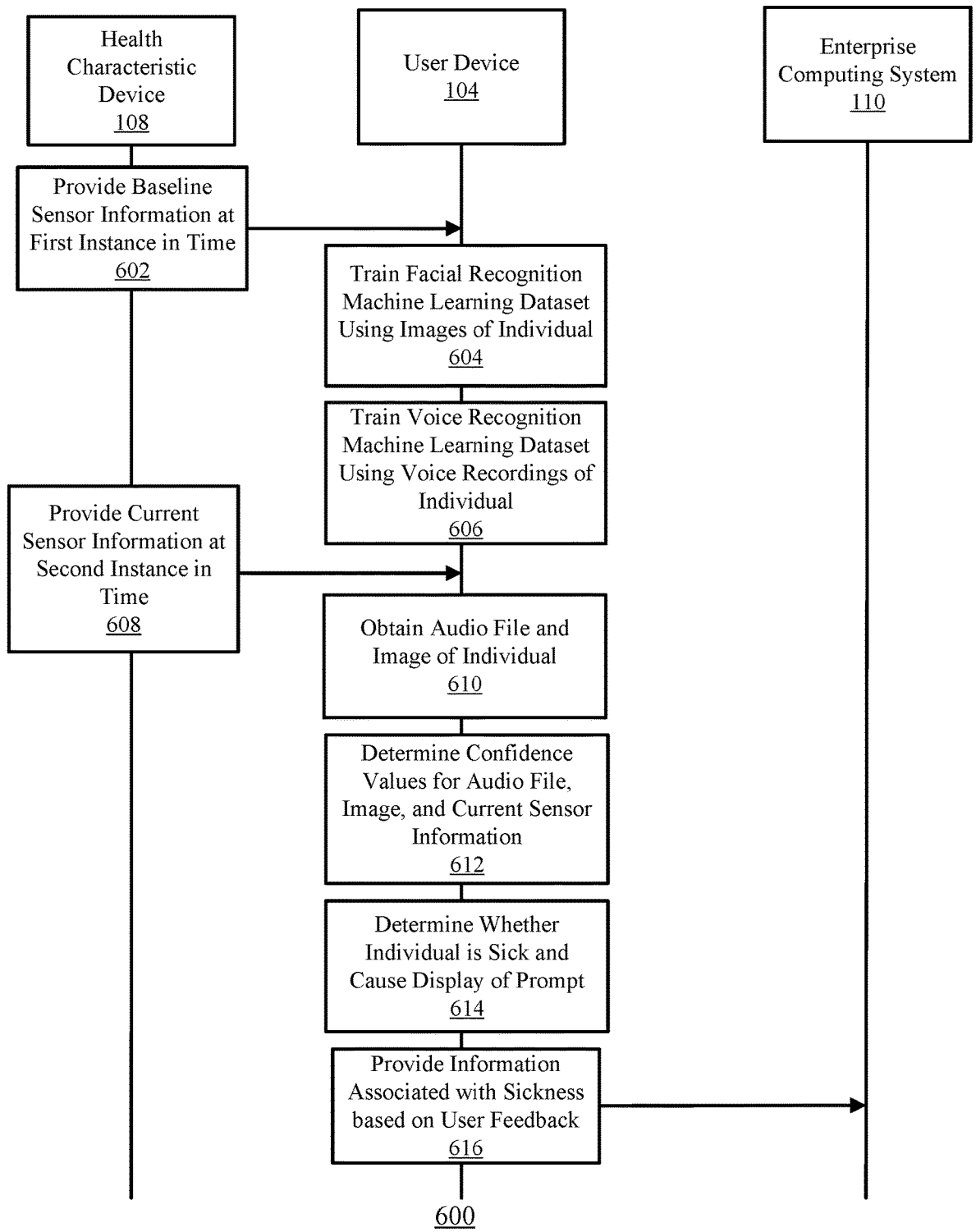
FIG. 6 is an exemplary event sequence for using machine learning datasets to determine whether an individual is sick in accordance with one or more exemplary embodiments of the present application.

FIG. 6 shows an exemplary event sequence 600 for using machine learning datasets to determine whether an individual is sick in accordance with one or more exemplary embodiments of the present application. However, the event sequence 600 is merely an example and other types of event sequences are contemplated herein including by performing any of the following blocks in any suitable order.

At block 602, the health characteristic device 108 may provide baseline sensor information (e.g., baseline oxygen level, heart/pulse rate, body temperature, and humidity of the individual 102) to the user device 104 at a first instance in time. The user device 104 may store the baseline sensor information in memory. Additionally, and/or alternatively, as mentioned above, the health characteristic device 108 and/or the user device 104 may update the baseline sensor information (e.g., based on abnormal readings of the sensor information over a period of time).

At block 604, the user device 104 may train the facial recognition machine learning dataset using images of the individual 102. At block 606, the user device 104 may train the voice recognition machine learning dataset using voice recordings of the individual 102.

The user device 104 may use the trained machine learning datasets and the baseline sensor information to determine whether the individual 102 is sick at a second instance in time. For instance, at block 608, the health characteristic device 108 may provide current sensor information to the user device 104 at the second instance in time. At block 610, the user device 104 may obtain an audio file including a voice recording of the individual and an image (e.g., facial image) of the individual 102. This may be performed similarly to blocks 402 and 404 described above. At block 612, the user device 104 may determine confidence values for the audio file, the image, and the current sensor information. This may be performed similarly to blocks 406 and 408 above. At block 614, the user device 104 may determine whether the individual 102 is sick and cause display of a prompt. This may be performed similarly to blocks 410 and 412 above. At block 616, the user device 104 may provide information associated with the sickness based on user feedback. For instance, after determining the individual 102 is sick, the user device 104 may display a prompt asking whether the individual 102 would like to alert another person such as the individual's boss, co-worker, and/or physician. The user device 104 may provide information including the indication that the individual 102 is sick as well as location data to the enterprise computing system 110. Using this information, the enterprise computing system 110 may provide information to another device/system/API indicating the individual 102 is sick.

In some instances, the health characteristic device 108 may perform one or more blocks of process 400 above in determining whether the individual 102 is sick. In other words, the health characteristic device 108 may train the facial/voice recognition machine learning datasets and use these machine learning datasets to determine whether the individual 102 is sick. Afterwards, the health characteristic device 108 may provide the indication to the user device 104 and/or the enterprise computing system 110. For example, examples of devices (e.g., the health characteristic device 108) capable of using machine learning datasets to determine health conditions (e.g., whether the individual 102 is sick) are described in further detail in U.S. patent application Ser. No. 16/886,464 (Titled: SYSTEMS AND METHODS FOR DETERMINING AND USING HEALTH CONDITIONS BASED ON MACHINE LEARNING ALGORITHMS AND A SMART VITAL DEVICE), filed on May 28, 2020, which is incorporated by reference herein in its entirety.

In some examples, the user device 104 may use any type of machine learning dataset and/or algorithm (e.g., supervised artificial intelligence algorithms, unsupervised artificial intelligence algorithms, and/or deep learning algorithms) to determine whether the individual 102 is sick. In some instances, the user device 104 may train and/or update this machine learning dataset and/or algorithm. For example, the user device 104 may obtain data such as facial images of the individual 102, images of another body part of the individual 102, and/or voice recordings of the individual 102 uttering a phrase (e.g., "Mary had a little lamb"). The user device 104 may prepare the data (e.g., standardize it) and/or otherwise re-format the data such that it is able to be used to train the machine learning dataset. The user device 104 may split the data into training data and test data. Then, the user device 104 may train the machine learning dataset using the training data to reach a target. For example, the user device 104 may train the machine learning dataset by determining whether the training data is continuous or discreet and/or using one or more regression/classification algorithms After training the dataset, the user device 104 may test the trained model using the test data. The user device 104 may perform another continuous or discreet analysis and render a decision. Finally, after the machine learning dataset is trained, the user device 104 may use the trained dataset to determine whether the individual 102 is sick (e.g., using the trained facial/voice recognition machine learning datasets to determine whether the individual 102 is sick).

A number of implementations have been described. Nevertheless, it will be understood that additional modifications may be made without departing from the scope of the inventive concepts described herein, and, accordingly, other examples are within the scope of the following claims. For example, it will be appreciated that the examples of the application described herein are merely exemplary. Variations of these examples may become apparent to those of ordinary skill in the art upon reading the foregoing description. The inventor expects skilled artisans to employ such variations as appropriate, and the inventor intends for the application to be practiced otherwise than as specifically described herein. Accordingly, this application includes all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the application and does not pose a limitation on the scope of the application unless otherwise claimed. No language in the specification should be construed as indicating any non-claimed element as essential to the practice of the application.

The invention claimed is:

1. A user device, comprising:
one or more processors; and
a non-transitory computer-readable medium having processor-executable instructions stored thereon, wherein the processor-executable instructions, when executed, facilitate:
receiving, from a wearable device and at a first instance in time, first sensor information indicating first health characteristics associated with an individual;
generating a baseline health model of the individual based on the first sensor information;
obtaining a facial image of the individual;
obtaining an audio file comprising a voice recording of the individual;
determining a facial recognition confidence value associated with whether the individual is sick based on inputting the facial image into a facial recognition machine learning dataset that is individualized for the individual;
determining a voice recognition confidence value associated with whether the individual is sick based on inputting the audio file into a voice recognition machine learning dataset that is individualized for the individual;
determining whether the individual is sick based on the baseline health model, the facial recognition confidence value, and the voice recognition confidence value; and
causing display of a prompt indicating whether the individual is sick.

2. The user device of claim 1, further comprising:
an image capturing device, and
wherein the processor-executable instructions, when executed, further facilitate:
using the image capturing device to obtain training data comprising a plurality of facial images of the individual; and
individualizing the facial recognition machine learning dataset for the individual based on training the facial recognition machine learning dataset using the plurality of facial images of the individual.

3. The user device of claim 1, further comprising:
a voice recording device, and
wherein the processor-executable instructions, when executed, further facilitate:
using the voice recording device to obtain training data comprising a plurality of voice recordings of the individual; and
individualizing the voice recognition machine learning dataset for the individual based on training the voice recognition machine learning dataset using the plurality of voice recordings of the individual.

4. The user device of claim 1, wherein the processor-executable instructions, when executed, further facilitate:
receiving, from the wearable device and at a second instance in time that is subsequent to the first instance in time, second sensor information indicating second health characteristics associated with the individual; and
determining one or more health characteristic confidence values based on comparing the second sensor information with the generated baseline health model,
wherein determining whether the individual is sick is further based on the one or more health characteristic confidence values.

5. The user device of claim 4, wherein the first and second health characteristics comprises one or more of an oxygen level of the individual, a temperature reading of the individual, a pulse rate of the individual, and a humidity value associated with the individual.

6. The user device of claim 1, wherein the processor-executable instructions, when executed, further facilitate:
receiving, from the wearable device and at a third instance in time, third sensor information indicating third health characteristics associated with the individual;
based on comparing the third health characteristics with the first health characteristics, causing display of a second prompt requesting user feedback associated with updating the baseline health model; and
in response to the user feedback indicating for the baseline health model to be updated, updating the baseline health model using the third health characteristics.

7. The user device of claim 1, wherein determining the facial recognition confidence value comprises:
inputting the facial image into the facial recognition machine learning dataset to determine a preliminary facial recognition value; and
calculating the facial recognition confidence value based on the preliminary facial recognition value and a facial recognition weighted value, and
wherein determining the voice recognition confidence value comprises:
inputting the audio file into the voice recognition machine learning dataset to determine a preliminary voice recognition value; and
calculating the voice recognition confidence value based on the preliminary voice recognition value and a voice recognition weighted value.

8. The user device of claim 7, wherein the processor-executable instructions, when executed, further facilitate:
determining, based on second sensor information from the wearable device, a preliminary sensor information value, wherein the preliminary sensor information value is associated with an oxygen level of the individual, a temperature reading of the individual, a pulse rate of the individual, or a humidity value associated with the individual;
calculating a health characteristic confidence value based on the preliminary sensor information value and a health characteristic weighted value, and
wherein determining whether the individual is sick is further based on the health characteristic confidence value.

9. The user device of claim 8, wherein the processor-executable instructions, when executed, further facilitate:
providing, to an enterprise computing system, a request for a plurality of weighted values associated with a particular type of illness; and
receiving, from the enterprise computing system, the voice recognition weighted value associated with the particular type of illness, the health characteristic weighted value associated with the particular type of illness, and the facial recognition weighted value associated with the particular type of illness.

10. The user device of claim 1, further comprising:
an image capturing device, and
wherein the processor-executable instructions, when executed, further facilitate:
using the image capturing device to obtain a second image of a portion of the individual's body, wherein the portion of the individual's body is any bodily portion of the individual other the individual's face, and
wherein determining whether the individual is sick is further based on the second image of the portion of the individual's body.

11. The user device of claim 1, wherein the prompt requests user feedback indicating whether to provide information to an enterprise computing system, and
wherein the processor-executable instructions, when executed, further facilitate:
based on the user feedback, providing information indicating the individual is sick to the enterprise computing system, wherein the information comprises geographical coordinates associated with the user device.

12. A system, comprising:
a health characteristic device, comprising:
one or more first processors; and
a first non-transitory computer-readable medium having first processor-executable instructions stored thereon, wherein the first processor-executable instructions, when executed, facilitate:
obtaining current sensor information indicating current health characteristics associated with an individual; and
providing the current sensor information to a user device; and
the user device, wherein the user device comprises:
one or more second processors; and
a second non-transitory computer-readable medium having second processor-executable instructions stored thereon, wherein the second processor-executable instructions, when executed, facilitate:
obtaining a facial image of the individual;
obtaining an audio file comprising a voice recording of the individual;
determining a facial recognition confidence value associated with whether the individual is sick based on inputting the facial image into a facial recognition machine learning dataset that is individualized for the individual;
determining a voice recognition confidence value associated with whether the individual is sick based on inputting the audio file into a voice recognition machine learning dataset that is individualized for the individual;
determining whether the individual is sick based on the facial recognition confidence value, the voice recognition confidence value, and the current sensor information from the health characteristic device; and
causing display of a prompt indicating whether the individual is sick.

13. The system of claim 12, wherein the first processor-executable instructions, when executed, further facilitate:
obtaining first sensor information indicating first health characteristics associated with the individual; and
providing the first sensor information to the user device, and
wherein the second processor-executable instructions, when executed, further facilitate:
generating a baseline health model of the individual based on the first sensor information,
wherein determining whether the individual is sick is further based on comparing the current sensor information with the baseline health model.

14. The system of claim 13, wherein the first and current sensor information comprises one or more of an oxygen level of the individual, a temperature reading of the individual, a pulse rate of the individual, and a humidity value associated with the individual.

15. The system of claim 13, wherein the first processor-executable instructions, when executed, further facilitate:
obtaining third sensor information indicating third health characteristics associated with the individual; and
providing the third sensor information to the user device, and
wherein the second processor-executable instructions, when executed, further facilitate:
updating the baseline health model of the individual based on the third sensor information,
wherein determining whether the individual is sick is further based on comparing the current sensor information with the updated baseline health model.

16. A method, comprising:
receiving, from a wearable device and at a first instance in time, first sensor information indicating first health characteristics associated with an individual;
generating a baseline health model of the individual based on the first sensor information;
obtaining a facial image of the individual;
obtaining an audio file comprising a voice recording of the individual;
determining a facial recognition confidence value associated with whether the individual is sick based on inputting the facial image into a facial recognition machine learning dataset that is individualized for the individual;
determining a voice recognition confidence value associated with whether the individual is sick based on inputting the audio file into a voice recognition machine learning dataset that is individualized for the individual;
determining whether the individual is sick based on the baseline health model, the facial recognition confidence value, and the voice recognition confidence value; and
causing display of a prompt indicating whether the individual is sick.

17. The method of claim 16, further comprising:
obtaining training data comprising a plurality of facial images of the individual; and
individualizing the facial recognition machine learning dataset for the individual based on training the facial recognition machine learning dataset using the plurality of facial images of the individual.

18. The method of claim 16, further comprising:
obtaining training data comprising a plurality of voice recordings of the individual; and
individualizing the voice recognition machine learning dataset for the individual based on training the voice recognition machine learning dataset using the plurality of voice recordings of the individual.

19. The method of claim 16, wherein determining the facial recognition confidence value comprises:

inputting the facial image into the facial recognition machine learning dataset to determine a preliminary facial recognition value; and calculating the facial recognition confidence value based on the preliminary facial recognition value and a facial recognition weighted value, and wherein determining the voice recognition confidence value comprises:

inputting the audio file into the voice recognition machine learning dataset to determine a preliminary voice recognition value; and calculating the voice recognition confidence value based on the preliminary voice recognition value and a voice recognition weighted value.

20. A method, comprising:

obtaining a facial image of an individual;

obtaining an audio file comprising a voice recording of the individual;

determining a facial recognition confidence value, wherein determining the facial recognition confidence value comprises:

inputting the facial image into a facial recognition machine learning dataset that is individualized for the individual to determine a preliminary facial recognition value; and calculating the facial recognition confidence value based on the preliminary facial recognition value and a facial recognition weighted value;

determining a voice recognition confidence value, wherein determining the facial recognition confidence value comprises:

inputting the audio file into a voice recognition machine learning dataset that is individualized for the individual to determine a preliminary voice recognition value; and calculating the voice recognition confidence value based on the preliminary voice recognition value and a voice recognition weighted value;

determining, based on sensor information from a wearable device, a preliminary sensor information value, wherein the preliminary sensor information value is associated with an oxygen level of the individual, a temperature reading of the individual, a pulse rate of the individual, or a humidity value associated with the individual;

calculating a health characteristic confidence value based on the preliminary sensor information value and a health characteristic weighted value;

determining whether the individual is sick based on the health characteristic confidence value, the facial recognition confidence value, and the voice recognition confidence value; and causing display of a prompt indicating whether the individual is sick.

21. The method of claim 20, further comprising:

providing, to an enterprise computing system, a request for a plurality of weighted values associated with a particular type of illness; and receiving, from the enterprise computing system, the voice recognition weighted value associated with the particular type of illness, the health characteristic weighted value associated with the particular type of illness, and the facial recognition weighted value associated with the particular type of illness.

22. The method of claim 20, further comprising:

obtaining, using an image capturing device, training data comprising a plurality of facial images of the individual; and individualizing the facial recognition machine learning dataset for the individual based on training the facial recognition machine learning dataset using the plurality of facial images of the individual.

23. The method of claim 20, further comprising:

obtaining, using a voice recording device, training data comprising a plurality of voice recordings of the individual; and individualizing the voice recognition machine learning dataset for the individual based on training the voice recognition machine learning dataset using the plurality of voice recordings of the individual.

24. The method of claim 20, wherein the prompt requests user feedback indicating whether to provide information to an enterprise computing system, and wherein the method further comprises:

providing, based on the user feedback, information indicating the individual is sick to the enterprise computing system, wherein the information comprises geographical coordinates associated with the individual.

* * * * *